United States Patent [19]

Adelman

[11] 4,419,544

[45] Dec. 6, 1983

[54] SIGNAL PROCESSING APPARATUS

[76] Inventor: Roger A. Adelman, Cincinnati, Ohio

[21] Appl. No.: 371,584

[22] Filed: Apr. 26, 1982

[51] Int. Cl.$^3$ ............................................. H04R 25/00
[52] U.S. Cl. ................................. 179/107 FD; 381/94
[58] Field of Search ............ 179/1 P, 107 R, 107 FD; 128/789, 784

[56] References Cited

U.S. PATENT DOCUMENTS 3,385,937  5/1968  Lacon ........................... 179/107 FD
4,366,349 12/1982  Adelman ....................... 179/107 FD

FOREIGN PATENT DOCUMENTS

2,613,513 10/1977 Fed. Rep. of Germany ...... 179/107 FD
5534560   3/1980 Japan ............................ 179/107 FD Primary Examiner—G. Z. Rubinson
Assistant Examiner—L. Schroeder
Attorney, Agent, or Firm—King and Liles

[57] ABSTRACT

A generalized signal processing device for use as a hearing aid generates and modifies signals representative of acoustic patterns in a physiologically compatible manner which enables persons suffering from various auditory pathologies to recognize sound patterns including human speech.

7 Claims, 12 Drawing Figures

NON-LINEAR AMP.

SIGNAL PROCESSING APPARATUS

BACKGROUND

This invention relates generally to hearing aids and more particularly concerns a method and apparatus for improving hearing communication in persons with various hearing deficits. The invention will be disclosed in connection with a generalized signal processing unit which restores meaningful neural patterns to the auditory recognition centers of the brain in a manner which enables persons and other higher animals to recognize a variety of sounds including human speech.

The present invention is derived from an understanding of the physiological processes of the normal hearing apparatus, and the manner in which the auditory system is compromised in conditions of hearing loss. The hearing apparatus in humans and higher animals consists of mechanical parts which transmit acoustic pressure waves from the air to the sensory neural network. The function and pathologies of the conductive portion of the hearing apparatus are well known up to the point of the mechanical-to-neural transduction site.

The mechanical-to-neural transformation occurs within the cochlea along a structure called the basilar membrane. This membrane demonstrates excursions which have a position-to-tone relationship. A vast network of neural cells which are sensitive to displacement are disposed in rows along the length of the membrane. The membrane thus performs a spectral analysis on the incoming sound, directing various portions of the frequency spectrum along specific neural channels. The specific neural cells which are involved in this transduction process are called the inner and outer hair cells. The inner hair cells are in primary relationship with the nerves which ascend toward the brain while the outer hair cells are in primary relationship with nerves which carry information down from the brain. The exact functional role of these two neural hair cells types has not been conclusively proven. Applicant postulates that the role of the inner hair cell is that of a pure receptor, and that this cell initiates electrical signals along its neural channel to the brain when it is displaced as a result of the motion of the basilar membrane. It is further postulated that the outer hair cell exerts a control function on the inner hair cell, specifically that it alters the threshold of displacement which must be exceeded before an electrical response can be initiated along a given neural pathway. Hence the inner and outer hair cells comprise the sending and modifying functions of an adaptive control system. It follows that there is an adaptive portion to the hearing system, that it is responsible for the high degree of pitch discrimination in humans and higher animals, that disease processes affect both the receptor inner hair cells and the adaptive controller outer hair cells, and, finally, that the structure places physiological constraints on the remedial signal processing which can be performed by any hearing aid.

Conventional hearing aids serve as amplifiers of the auditory signal. The presentation of an amplified signal does provide a means for restoring the conductive functions of the ear. However, amplification alone is of only marginal help if the mechanical-to-neural structure has been damaged. In these cases the neural channels that carry specific frequencies to the brain and their contribution to the adaptivity function have been lost. Under extreme amplification, the excursion of the basilar membrane will be broad enough to excite adjacent hair cells, and if these cells exist, a signal will be sent to the brain.

However, the amplification does nothing to restore adaptivity, and the function of identifying important sounds from background noise can occur only with conscious effort at higher levels of the brain. Applicant postulates that this effort is fatiguing and is the reason why the adjustment period for a hearing aid user is difficult. In more advanced disease of the sensory-neural network, adjacent channels may not be present for stimulation by signals which are amplified to levels which can be physically damaging to the auditory structures. In these cases the portion of the frequency spectrum which has no neural channels must be readdressed to other still viable neural channels, and the adaptivity function belonging to the lost frequency portion must be performed external to the ear.

A variety of hearing aid devices have been proposed for addressing the problem of sensory-neural deafness. The methods and means of the previous methods have utilized band shifting of frequencies, various transformations of the auditory signal, alteration of the formant loci, and amplitude compression schemes. The methods fail to recognize the inseparability of the adaptive and receptor functions, and only address a part of the necessary signal processing functions which must be performed. Furthermore, the previous methods fail to recognize the highly individual nature of the hearing loss in any patient, and the need for the minimal but generalized signal processing to restore recognizable auditory patterns in the auditory cortex of the brain.

Accordingly, it is an objective of the present invention to provide new and useful methods and means for restoring recognizable auditory communication to persons having various deficits in their auditory sensory apparatus. It is another object of the present invention to define methods and means for the characterization of residual hearing function in terms of the spectral and adaptive portions of a signal processing system.

It is another objective of the present invention to provide a hearing aid system which performs signal processing on an auditory signal in a manner which compensates for the natural signal processing which is lost by the failure or destruction of parts of the normal auditory network.

It is another objective of the present invention to provide the means for automatically discriminating important information from noise in the auditory signal in an effort to restore the adaptive portion of the hearing function.

It is another objective of the present invention to provide the means for shifting, in a physiologically compatible manner, portions of the frequency spectrum of the auditory signal toward viable neural channels in the auditory organ system.

SUMMARY OF THE INVENTION

In accordance with one aspect of the invention, a signal processing apparatus is provided which receives a first acoustic signal and generates a second acoustic signal with a modified pattern in response to the first signal. The apparatus includes means for initially receiving the first acoustic signal and generating a representative processed signal. Portions of this generated signal which do not exceed a predetermined pattern recognition function are then suppressed by an adaptive noise cancelling means. The signal produced by the adaptive noise cancelling means is then amplified and converted into a modified acoustic signal.

According to a further aspect of the invention, a hearing aid includes a means for generating a processed signal representative of a received acoustic signal. This generated signal is applied to a frequency band separating means which divides the signal into at least two separated signals according to frequency. At least one of these sepatated signals is directed to a means for transposing the frequency content to higher or lower frequency ranges while maintaining the harmonic relationship characterizing the band separated signal. Further means are provided for temporally matching the band separated signals and for summing the temporally matched signals into a resultant signal which is, in turn, converted into a modified acoustic signal.

Yet another aspect of the invention relates to an apparatus for testing hearing capabilities in humans. The apparatus includes a means for receiving an acoustic signal and generating a responsive and representative processed signal. An adaptive noise cancelling means suppresses portions of the generated signal which do not exceed a predetermined pattern recognition function. This noise cancelling means also includes means to variably adjust the characteristics of the pattern recognition function as well as means to restrict the frequency content upon which the pattern recognition is performed. A variable frequency band separating means divides the correlated signal into a plurality of band limited output signals, each of which is directed to a circuit path with a non-linear amplifier for automatically greater amplifying the lower intensity portions of the signal while lesser amplifying its higher intensity portions. The non-linear characteristic of the amplifier is variable. The testing apparatus further includes means for selectively and variably transposing the frequency of the separated signals while maintaining the harmonic relationships of said separated signals.

BRIEF DESCRIPTION OF THE DRAWINGS

The above and other objects, features, and advantages of the present invention will become apparent from a consideration of the following detailed description presented in connection with the accompanying drawings in which.

DESCRIPTION OF THE PREFERRED EMBODIMENT

Figure 1:
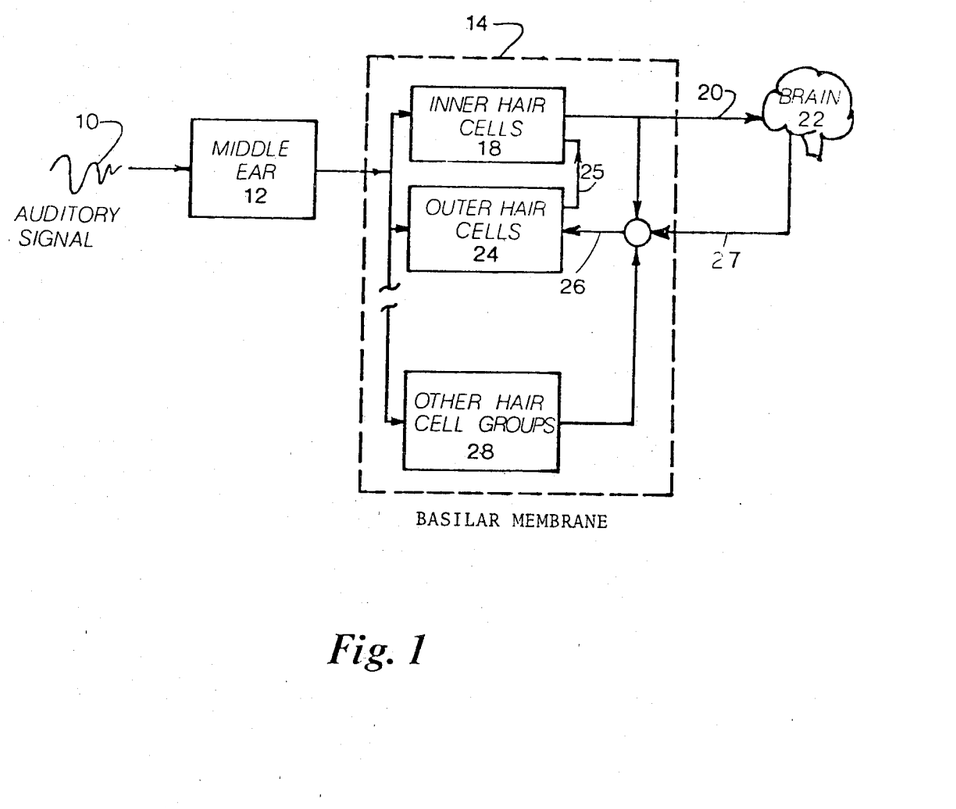
FIG. 1 shows a schematic depiction of the normal signal processing functions which comprise the human auditory system.

Referring now to the drawings and to FIG. 1 in particular, a schematic depiction of the normal signal processing functions of the human auditory system is shown. An auditory signal 10 is applied to the external ear and the conductive network of the middle ear as represented by box 12. In this portion of the system the acoustic pressure wave produced by the auditory signal is converted into movement of the mechanical structures of the middle ear. This mechanical movement is then transmitted to the basilar membrane of the inner ear depicted by box 14 in the illustration of FIG. 1. This mechanically responsive membrane 14 receives mechanical stimulus from the middle ear structures and causes a spectrally selective excitation of neural cells 18 commonly known as inner hair cells which are disposed along its expanse. On excitation, a portion of of these cells 18 transmit electrical impulses along ascending neural pathways 20 to the brain 22. A second portion of the neural signal 23 so generated, and a delayed, evoked neural signal 27 descending from the brain the brain produce an effect on yet another set of neural cells 24 commonly known as outer hair cells which are also located on the basilar membrane 14. The effect on the outer hair cells 24 produced by the combined neural and mechanical signals causes the modification indication by path 25 of the local electro-chemical environment of inner hair cell 18. The electro-chemical environment effects the threshold at which the inner hair cell responds to mechanical stimulus.

Mechanical motion of the basilar membrane in response to motion of the middle ear structures initially stimulates a plurality of both inner and outer hair cell groups located at positions of maximal excursion along the membrane. The portion of membrane which is elevated sufficiently to cause initial firing of the inner hair cells is relatively broad, and by itself cannot account for the tonal acuity which the auditory system demonstrates. A modification of the electro-chemical environment, as depicted as the process arrow 25 in the illustration, alters the threshold of the inner hair cells 18 and results in the local sharpening of the neural spectrum. This sharpened neural response establishes the bandwidth of pitch perception. A neural input 26 to the outer hair cells 24 acts in concordance with mechanical input to determine the stimulation of those cells. Signals on the neural input 26 are the summation of neural signals arising from the local inner hair cells 18, from other groups of hair cells 28, and from the brain 22. The other groups of hair cells 28 are located at points along the basilar membrane 14 which correspond to frequency spectral differences of approximately one-sixth of an octave. Applicant postulates that the contribution of the other groups of cells is to modify the activity of the outer hair cells 24, and results in enhanced sharpness.

The mechanical-to-neural portion of ear perceives bands of excitation which correspond to the hair cell groups in a manner analogous to the function of a spectrum analyzer. Thus the ear is comprised of a plurality of contiguous receptor/modifier channels each having primary responsibility for the interpretation of a particular segment or band of the frequency spectrum. Because the mechanical-to-neural transduction process is frequency responsive, a loss of selected hair cell groups will result in a correspondingly selective loss in the audio frequency range.

Figure 2A:
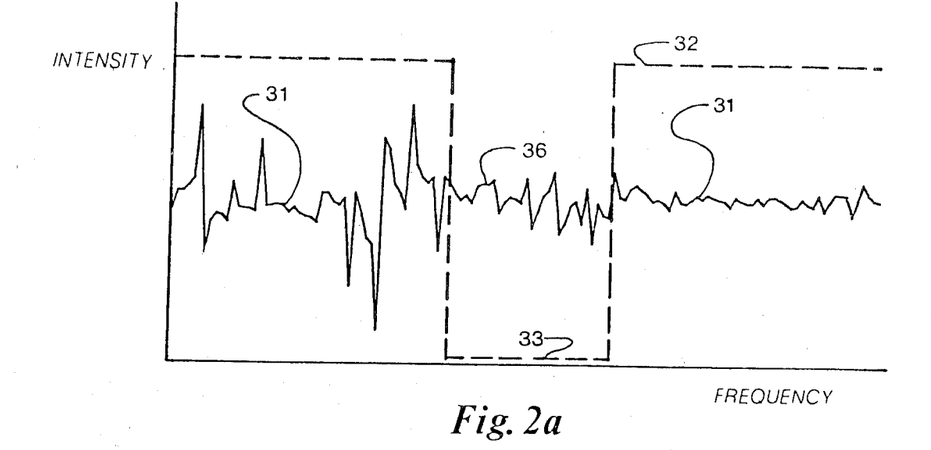
FIG. 2a depicts the frequency spectrum of a typical auditory signal and a schematized representation of the effect of a neural hearing loss on the auditory spectrum.

FIG. 2a depicts the frequency spectrum of a typical auditory signal as the solid line 31 with its intensity plotted on the ordinate versus its frequency plotted on the abscissa. The dashed line 32 of FIG. 2a represents the filter characteristic of a pathological ear with its low-valued portion 33 corresponding to the loss of hair cell groups. In the presence of pathologies affecting the hair cell groups, the functions of these components are lost. Hence both the receptor function of the inner hair cells and the modifying function of the outer hair cells fail. The result is twofold: first the primary signal cannot be presented to a viable neural ascending channel, and second the sharpening of the signal cannot occur. Under such pathological conditions, the lost original portion 36 of the frequency spectrum cannot be recovered by simple amplification because no viable neural channels exist for its reception.

Figure 2B:
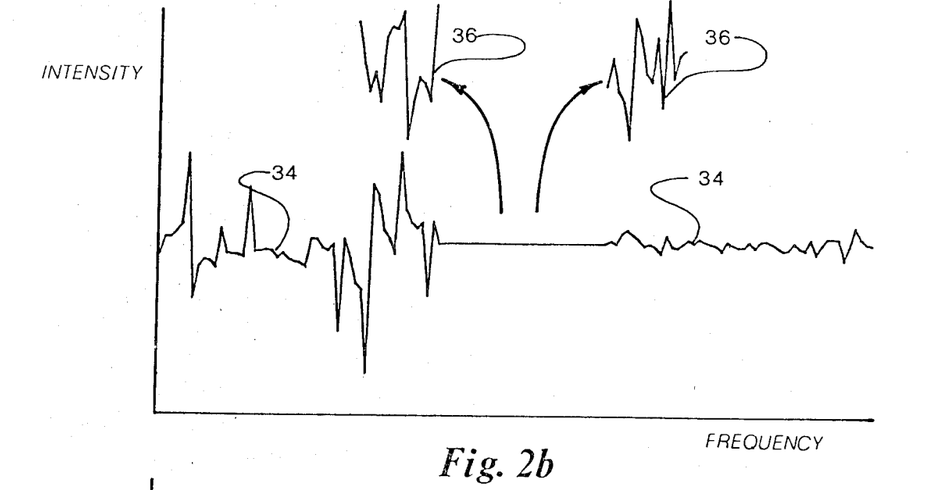
FIG. 2b depicts the movement of portions of the auditory spectrum from regions of hearing loss to higher and lower adjacent frequencies.
Figure 2C:
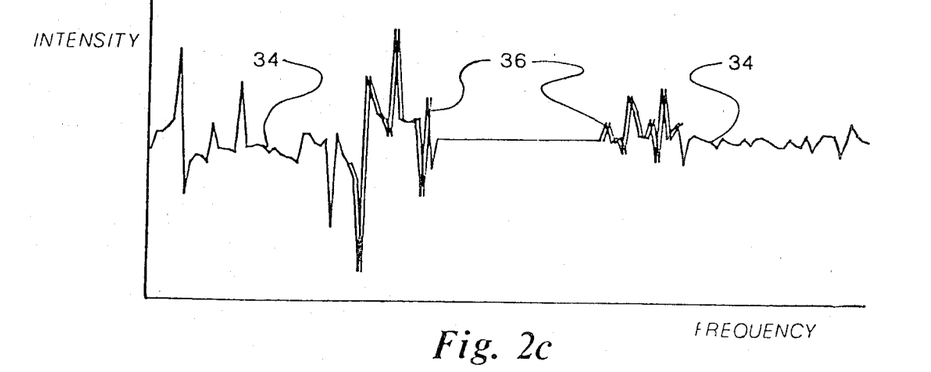
FIG. 2c depicts the summation of the so moved portions of signal with frequency portions of the signal which is addressed to viable portions of the neural auditory system.

FIG. 2b demonstrates the movement of the lost information 36 to viable neural channels. The information in the lost band is shifted upward and/or downward in frequency to be readdressed to the brain via hair cell groups which have remained intact. The so-called lost information 36 which has been so shifted in a physiologically appropriate manner is then added to the viable portions of the receptor spectrum 34 as shown in FIG. 2c.

Figure 3:
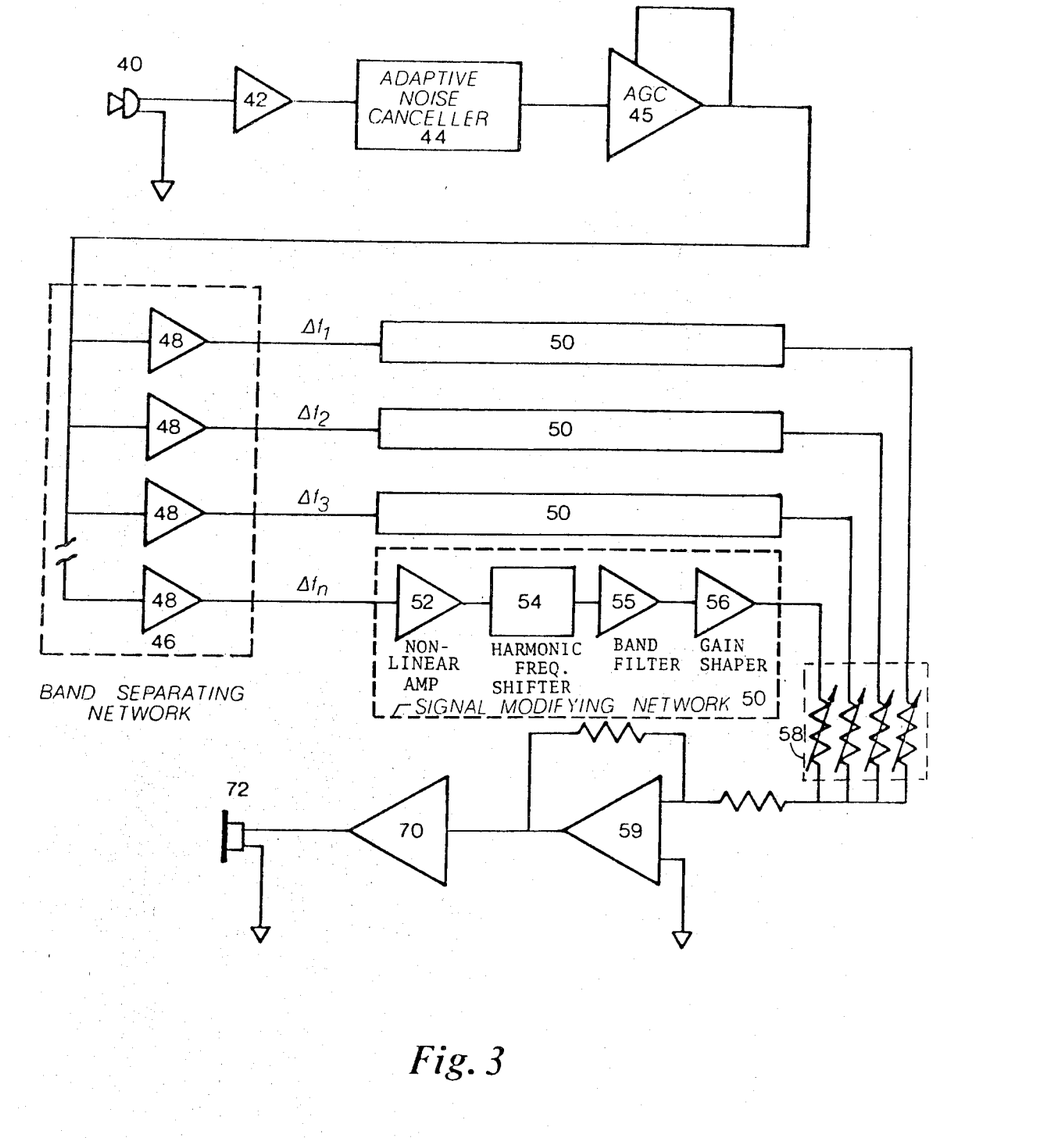
FIG. 3 is a schematic of a generalized signal processing apparatus made in accordance with the principles of the present invention.

A schematic depition of a generalized signal processing hearing aid apparatus is illustrated in FIG. 3. An audio signal is received by a microphone 40 which in turn provides an electrical signal to buffer amplifier 42. The output signal from buffer amplifier 42 is directed into an adaptive noise cancelling element 44 for the purpose of deleting or suppressing portions of the auditory signal which do not correlate or have a coincident pattern relationship with the strongest dominant frequency residing in a predetermined range. The resulting output signal produced by the adaptive noise canceller 44 is then applied to a fast attack and slow release type automatic gain control amplifier 45, the output of which is directed to a frequency band separating network 46. This network divides the signal by means of variable bandpass filters 48 according to frequency content and produces a plurality of signals each containing a variably selected portion of the frequency spectrum. Each of these variably selective portions of the signal spectrum is then input to one of a plurality of signal modification networks 50. Only one of the signal modification networks is shown in detail in the drawings, although the other represented networks 50 contain detail elements identical to those described in the sequel. The signal modification network 50 contains a nonlinear amplifier element 52, a harmonic frequency transposer element 54, a band filter element 55 and a gainshaping amplifier elements 56. The output of each of the signal modification networks 50 is input to a summing amplifier 59 through variable attenuating elements associated with each signal modification network 50 and collectively identified on the illustration by the numeral 58. Output from the summing amplifier 59 is directed to a power amplifier 70 having suitable impedance characteristics to match its output to an earpiece/speaker 72 for transmission to the patient's defective auditory system.

Figure 4:
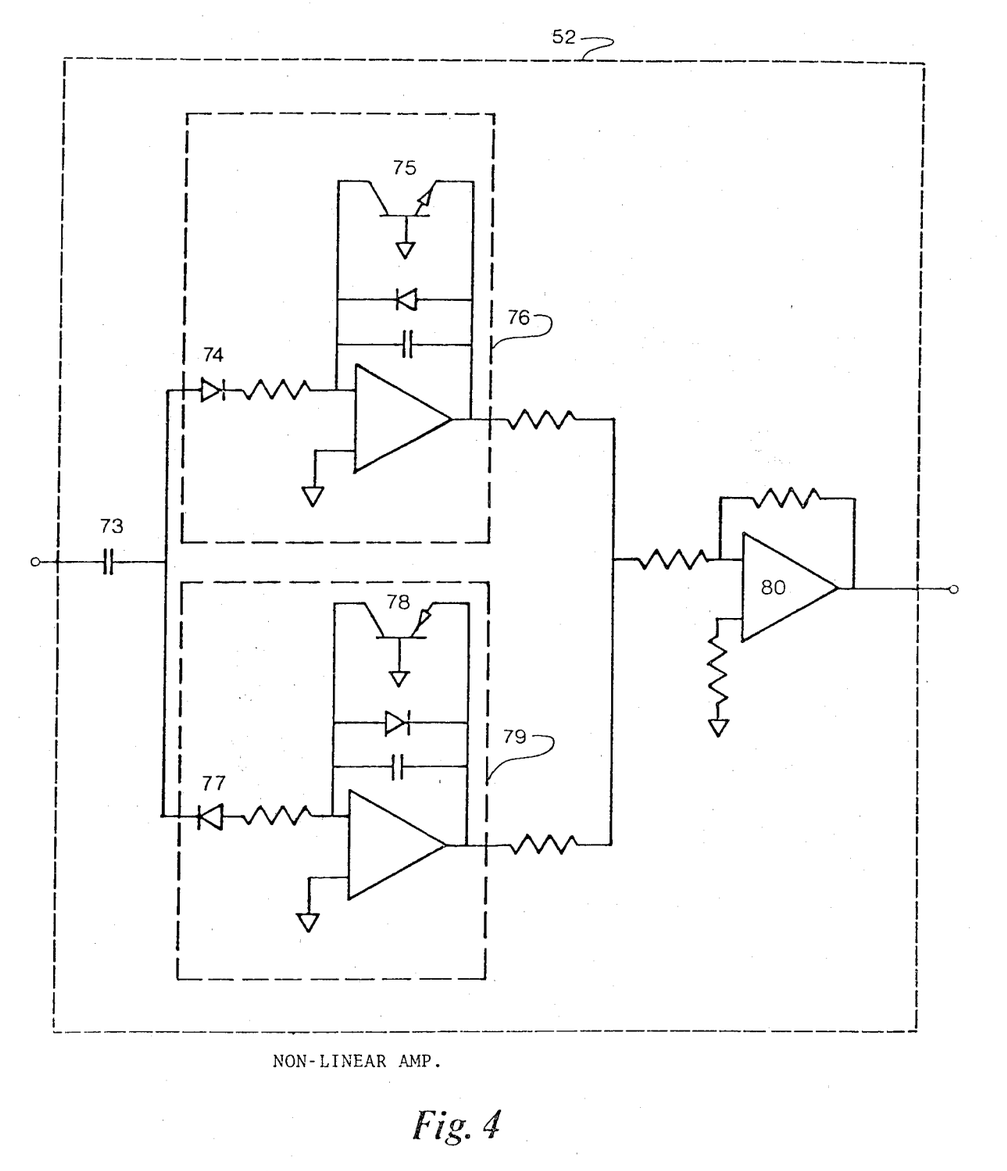
FIG. 4 is a detailed schematic of one embodiment of a practical electronic circuit for the nonlinear amplification element of the apparatus.

FIG. 4 illustrates one example of an amplifier system which can serve as the nonlinear amplifier element 52 identified in FIG. 3. The illustrated nonlinear amplifier element 52 is a double sided logarithmic type and includes an input decoupling capacitor 73 for removing the d.c. offset from the signal. The resulting signal is then divided into positive and negative portions by diodes 74 and 77 respectively. The positive portion of the signal is then caused to be processed through an amplifier stage 76 employing an NPN transistor feedback element 75 operating in its nonlinear region. Appropriate passive elements useful to the operation of the amplifier stages are also indicated in the illustration. A logarithmic output from the amplifier stage 76 is thus obtained for the positive portion of the signal. The negative portion of the signal is similarly processed by the logarithmic amplifier stage 79 employing a PNP transistor feedback element 78 operating in its nonlinear region. The positive and negative logarithmic output signals are then caused to be added together in the summing amplifier 80 to provide input for the harmonic transposition element shown in detail in FIG. 5.

Figure 5:
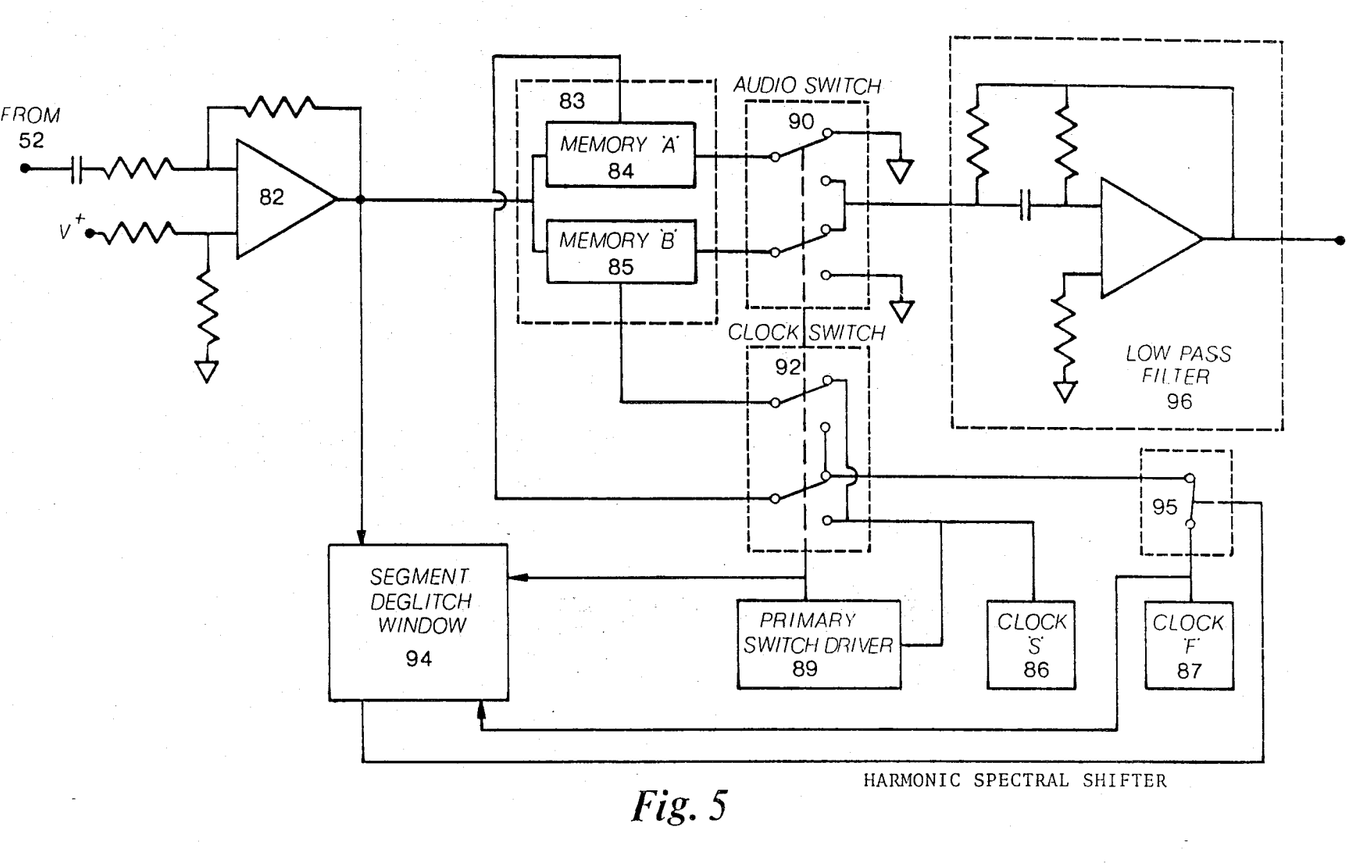
FIG. 5 is a detailed schematic of one embodiment of a practical electronic circuit for realizing the harmonic spectral shifting element of the apparatus.

FIG. 5 illustrates one embodiment of a harmonic transposition element 54 for the selective multiplication or division of all frequencies by a constant value. The movement of all frequencies by a multiplicative process retains the harmonic relationships which are present in the original signal. Because of the importance of the relationship of harmonics in the recognition of speech and other significant acoustic patterns, and because of the postulated role of harmonic contribution in the mechanical to neural transduction process at the hair cell level, only harmonic transposition is suitable for retention of information content in a form recognizable to the brain.

In the illustrated form depicted in FIG. 5, the output of the nonlinear amplifier 52 is applied to a time axis dividing, sampled signal, frequency harmonic transposition, system 54 through the agency of an input buffer and offset preamplifier 82. This element isolates the signal from previous stages and also adds a d.c. voltage. The d.c. offset voltage is necessary for the processing of the signal through a multi-element, storage component such as a conventional dual serial analog delay element 83. One such element is an SAD 1024 manufactured by the Reticon Corporation of Sunnyvale, Calif. The isolated and offset signal is then caused to be input to the discrete time serial analog memories contained in the serial analog element 83. The movement of the signal through each serial memory of the analog delay element 83 occurs in a "bucket brigade" fashion, with the signal being passed from one memory cell or "bucket" to the next on the command of a clock pulse. Independent clock pulses are provided to each memory to achieve different delays, or movements of "information buckets", in each memory delay line.

In operation, memory 'A' (84) is driven by timing pulses from a first clock 'F' 87 arriving through the agency of clock switch 92. The buffered, offset signal is input to memory 'A' as a string of sampled data as long as the fast clock interruptor switch 95 remains closed. The delayed output of memory 'A' is directed to ground through the agency of audio signal switch 90. The memory 'A' (84) as depicted in FIG. 5 is said to be in its input cycle. The contents of memory 'A' (84) thus represents a sampling of the signal with samples being taken at the frequency of clock 'F' 87. During the immediately previous positioning of the audio switch 90 and clock switch 92, memory 'B' (85) was filled in an identical manner. In the depicted position of the clock switch 92 and the audio switch 90, memory 'B' (85) is driven by timing pulses arriving from a second clock 'S' 86. The contents of memory 'B' (85) are output to the low pass filter 96 through the agency of audio switch 90. The memory 'B' (85) as depicted in FIG. 5 is said to be in its output cycle. After clock 'S' has generated the number of pulses exactly equal to the number of cells in the memory, primary switch driver 89 causes audio switch 90 and clock switch 92 to be moved into their other contact positions. This reverses the functions of the memories. In this way a memory may be loaded at the fast clock rate from clock 'F' 87 and unloaded at the relatively slower clock rate from clock 'S' 86, the result being an apparent division of all frequencies of the signal by a constant amount corresponding to the ratio of the slow to fast clock rates. The unload clock 'S' in each of the signal modification networks 50 are preferably synchronized and output at the same rate to provide temporal matching among the signals output from the various signal modification networks 50.

In general a portion of the signal must be discarded during the frequency division process because no alteration in the temporal period occurs; i.e. the inverse relationship between time and frequency of the signal is violated. As a result, discontinuities normally arise between the signal segments at each switching of the memory function. Circuitry contained in the segment deglitch window element 94 senses the attributes in the signal portions prior to switching, and provides means for minimizing such discontinuities. The segment deglitch window element 94 causes a moveable "window" of sample time by variably opening clock interruptor switch 95. The moveable time "window" is caused to stop when conditions are met which minimize discontinuities arising from the switching of the memory functions.

In a similar manner, well-known memory recirculation schemes may be employed to provide for a continuous signal generation and a variably moving window when a multiplication of the signal frequency is to be accomplished, i.e. when the ratio of the clock rates is greater than unity.

There are upper and lower restrictions on the delays which may be imposed on the audio circuit for hearing aid applications. These restrictions dictate the ranges for the clock frequencies and, secondarily, they restrict the range for the number of cells contained in the memories. These restrictions arise from sampling theory, linguistic, auditory sensitivity, and temporal bases. Signal theory requires that the sampling rate be at least twice the frequency of the highest frequency contained in the auditory signal and also that at least one complete cycle of the lowest frequency of the auditory signal be retained in the memory. Linguistic sensibility demands that the amount of information which is discarded be somewhat less than a phoneme time period. Auditory sensitivity requires that the sampling frequency lie above the frequency range for any individual, and it also requires that the discontinuities occur at the broadest time intervals. Finally, phonemic temporal restrictions require that the transposition be accomplished in as nearly "real time" as is possible. This last restriction is imposed to preserve lip synchronization, and is particularly important to persons with hearing deficit. A suitable set of parameters for the depicted circuit provides an intermediate delay of 10 to 60 milliseconds using clock frequencies in the 15 kHz range and 512 memory cells. These parameters insure that within a linguistically distinct period there will be temporal matching of the signal.

Figure 6A:
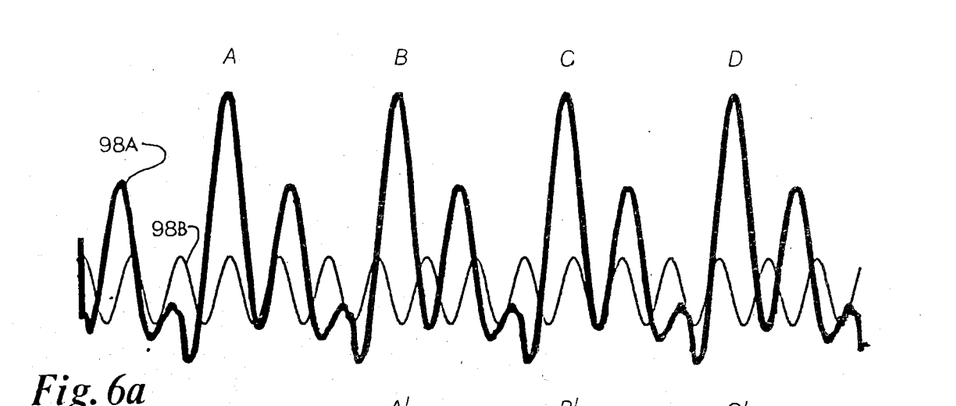
FIG. 6a depicts a typical auditory signal of repetitive time period and varying amplitudes in the presence of a competing but lower amplitude periodic noise signal.
Figure 6B:
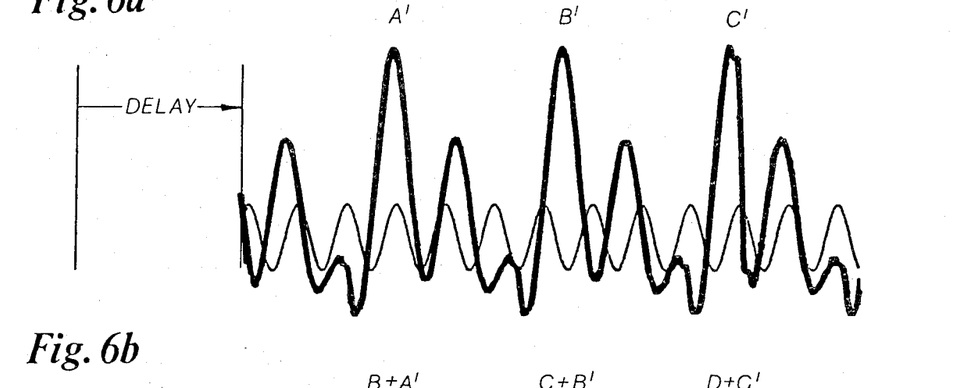
FIG. 6b depicts the signal presented in FIG. 6a as delayed in time by one major time period of the auditory signal.
Figure 6C:
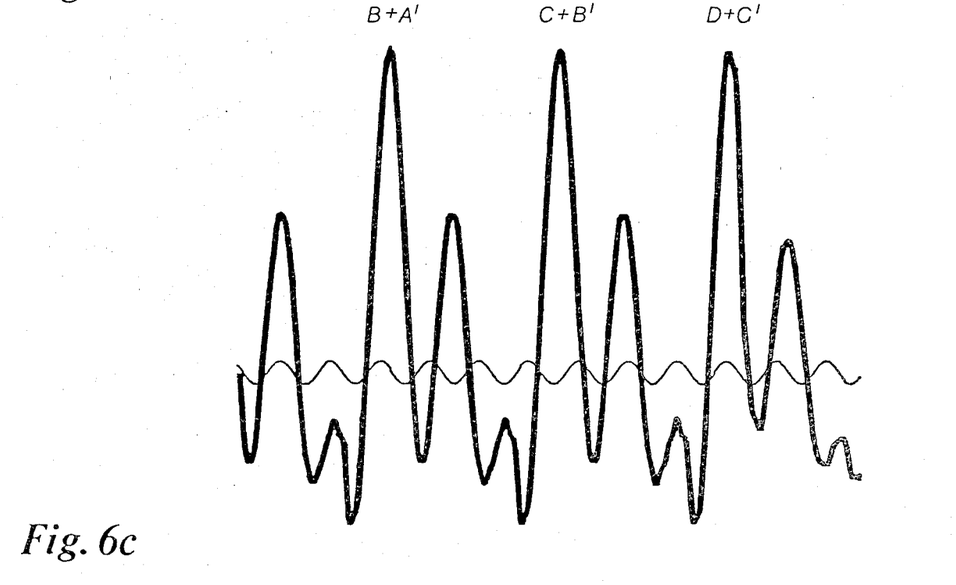
FIG. 6c depicts the noise cancelling effect of summing a signal delayed by one major time period of the auditory signal with a non-delayed signal of similar shape.

FIGS. 6a, 6b, and 6c are an expository representation of the function of the suppression of noise from "meaningful" auditory signals. The preselection of a "meaningful" auditory signal is postulated on the notion that speech arises from a vibrating source having a fundamental frequency of less than 500 Hz, and that the modifications or formants which convert the vibrations into linguistic patterns are correlated with the fundamental or a low harmonic of the vibrating sound source. In general, the competing noise will not have periods which coincide with the period or multiples of the period of the "meaningful" auditory signal.

In the representation of FIG. 6a, a "meaningful" auditory signal, as shown by the heavy line 98a, consists of four periods 'a', 'b', 'c', and 'd' of primary information plus some uncorrelated noise signal represented by the light, sinusoidal line 98b. A time-shifted version of the signals 98a and 98b is depicted in FIG. 6b wherein the time shift corresponds to exactly one time period of the auditory signal. The depicted signal retains three of the original four periods of the auditory signal. If the signals of FIG. 6a and FIG. 6b are added together they form a new signal as shown in FIG. 6c which reinforces the primary signal and all signals which have time correlates with it, while simultaneously suppressing all non-correlated noise signals.

Figure 7:
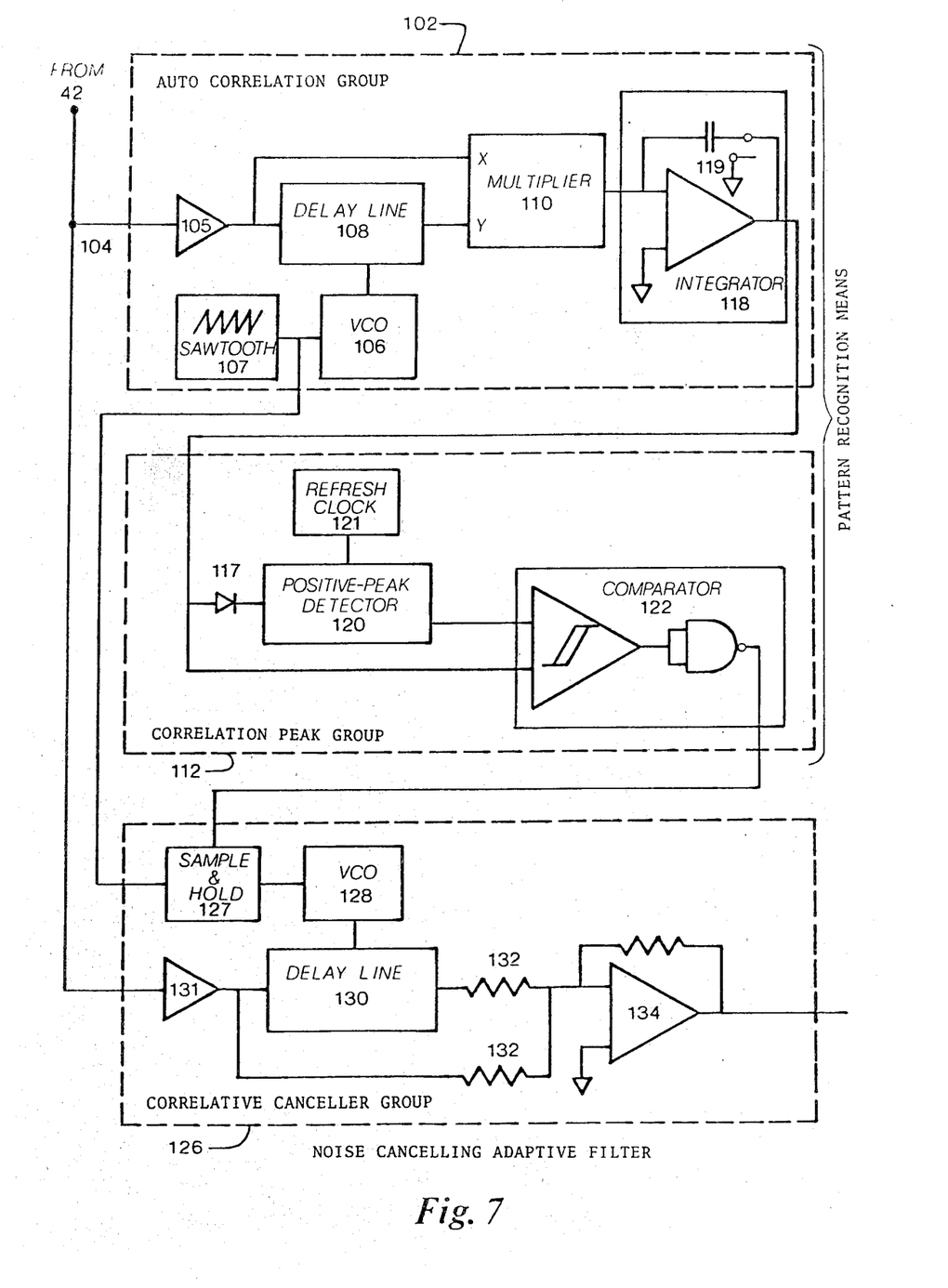
FIG. 7 is a detailed schematic of one embodiment of a practical electronic circuit for realizing the noise cancelling adaptive filter element of the apparatus.

FIG. 7 illustrates one embodiment of an adaptive noise canceller element 44 for the suppression of noise signals from meaningful auditory input. The illustrated means is based on the correlative principles demonstrated in FIGS. 6a, 6b, and 6c. Within the element are functional blocks which constitute an autocorrelation group 102, a correlation peak group 112, and a correlative canceller group 126. In the depicted preferred embodiment, auto correlation group 102, and peak correlation group 112 together constitute a pattern recognition means. Said means enables the periodic "locking" of a quasi-static signal with a delayed version of itself in the correlative canceler group 126. If the signal is a pure sinusoid, the elements 102, 112 and 126 perform the function of a simple phase locked loop. Similarly, if the pattern recognition requirements of the system are relaxed to require the recognition of only a single frequency, the depicted circuitry may be degenerated to constitute a simple phase locked loop.

Operatively, the auditory signal which has been processed by buffer amplifier 42 of FIG. 3 is caused to enter a splitting junction 104 where it is directed to both the autocorrelative group 102 and the correlative canceller group 126. Within the autocorrelation group 102 the auditory signal is applied to a bandpass buffer amplifier/filter 105 and thereafter to both a delay line 108 and to the 'X' input of a multiplier module 110. The buffer amplifier/bandpass filter facilitates the selection of the correlation on a particular frequency portion of the original signal. The delay line 108 consists of a number of sequential storage elements which cause the signal to be passed from element to element on a clock signal. The clock signal is provided by a voltage controlled oscillator 106 whose output frequency is caused to vary linearly in response to the output of a sawtooth waveform generator 107. The portion of the signal passing through the delay line 108 is directed to the 'Y' input of the multiplier module 110. The product of the nondelayed portion of the signal and the portion of the signal which has undergone the variable delay is then directed to an integrator circuit 118. Output from the integrator 118 corresponds to a short-time auto-correlation function:

$$\int_{t1}^{t2} f(t)f(t-x)dt = \text{AUTOCORR}[f(t)]$$

The time period of the correlation function is determined by the sawtooth characteristics of the voltage which controls the oscillator 106 and the integrator circuit switch 119 characteristics. In the preferred embodiment, the period is set to substantially correspond to the fundamental and first harmonic frequencies of human speech. The correlation function will achieve a positive maximum value when the delayed signal has been retarded by one period as depicted in FIG. 6b.

The correlation signal is then directed to the correlation peak group 112 where the time period between repetitive portions of the auditory signal is determined. The correlation signal is directed through diode 117 to a positive peak detector module 120. The peak detector module 120 determines the value of the highest power over a composite time period. This composite time period is determined by the correlation function period, the integrator time constant, and a third time restriction provided by a refresh clock 121. The refresh clock 121 prohibits the peak energy which occurs during one portion of a word from being compared with a lesser power exhibited at a linguistically temporally distant time. For example, the time between the sounds "pow" and "er" in the word "power" would be functionally separated by the refresh clock 121. Output from the positive peak detector 120 and output from the integrator 118 are directed into the input of a comparator circuit 122 which produces a logical HI state when the values of the peak detector 120 and the integrator 118 are nearly identical. A hysteresis type of comparator suppresses the tendency to change the states of the output in an unstable fashion. The comparator 122 produces a logical valued output through the agency of a NAND device. In operation, when the current value of the output of the autocorrelation group 102 and the value of the peak detector 120 are nearly equal, the autocorrelation function is near its optimal time delay. The resulting logical HI state thus produced on the comparator 122 is used to "hold" the instantaneous value of the sawtooth waveform generator 107 in the sample and hold circuit 127. This voltage then holds the delay line clock 128 at a constant frequency and, in turn, produces a delay in the portion of the auditory signal passing through delay line 130 equivalent to one period of the primary frequency of the auditory signal. The upper and lower clock frequencies are predetermined by the sound environment and individual hearing loss characteristics of the hearing aid wearer.

The auditory signal which has been directed from buffer amplifier element 42 of FIG. 3 into the correlative canceller group 126 first passes through buffer amplifier 131 and then is caused to follow two pathways through the circuitry of the correlative canceller group 126. One of these paths goes through the delay line 130 which retards its progress by one period of the primary frequency of the auditory signal through the means described previously. The other path is a simple undelayed transmission line. The undelayed and the delayed portions of the signal are then caused to pass through balancing resistors 132 after which they are added together in the summing amplifier 134 wherein the signal attains the characteristics depicted in FIG. 6c.

Figure 8:
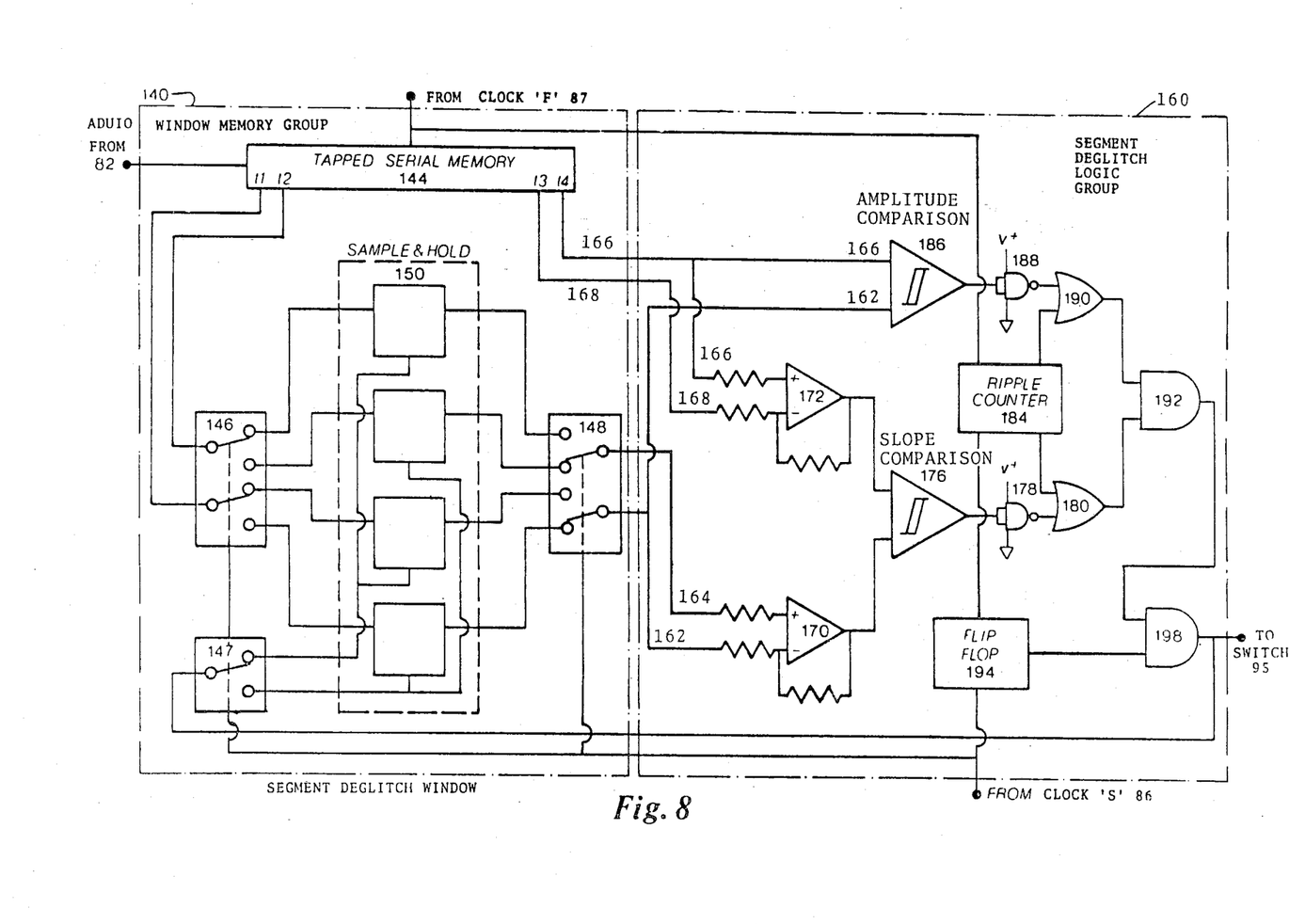
FIG. 8 is a detailed schematic of one embodiment of a practical electronic circuit for realizing the segment deglitch window element of the apparatus.

FIG. 8 illustrates one embodiment of a segment deglitch window element 94 for the minimization of transitional discontinuities arising from the joining of originally discontiguous signal segments. The illustrated method is based on the concept of the movement of a time "window" over the portion of the signal which is to become the next segment loaded into memory. Within the element are functional blocks which constitute an auxilliary window memory group 140 and a segment deglitch logic group 160.

Operatively, the window memory group 140 provides means for determining the values of trailing portions of a first signal segment and the values of the leading portions of a next signal segment. A sequential memory element 144 receives a continuous signal from the buffer offset amplifier 82 of FIG. 5. The signal is then sampled and caused to advance sequentially through the memory by the agency of clocked pulses arising from clock 'F' 87 of FIG. 5. Intermediate "taps" are provided along the memory at the locations of the lowest and second lowest, as well as the highest and second highest memory addresses. The value of the sample residing in each of these addresses is thus available through the agency of the appropriate tap.

The samples residing in the lowest and second lowest memory addresses are directed to switch 146 where they are each directed to an element of the multiple sample and hold network 150. Each of the storage elements in the sample and hold network 150 will hold the instantaneous value of its input signal upon the application of the sequence of a logical low followed by a logical high value on the set/reset. The sample and hold element will continue to hold the said value until a low-high sequence is again applied. The appropriate logic values are applied alternately to pairs of the sample and hold elements through the agency of switch 147 which derives its logic values from output of the circuitry of segment deglitch logic group 160. The values residing on the storage elements are brought out in alternating pairs through the agency of switch 147. The switches 146, 147 and 148 are caused to change state in accordance with a signal provided by the primary switch driver 89 of FIG. 5. The output of switch 148 thus provides the last and the next to last value of the previous signal segment on lines 162 and 164 respectively. The values of the first and second samples of the new signal segment are taken directly from the highest and next highest memory addresses of auxiliary memory 144. The first value is presented on signal line 166, and the second value is presented on signal line 168.

The segment deglitch logic group 160 utilizes the information provided by the window memory group 140 to perform a hierarchy of logical decisions. These decisions determine the starting position of signal segment which is to follow the signal segment which is immediately in its output function. The decisions provide, in order, that (1) a completely full complement of samples will be available in the memory when it is switched to its output function; (2) the amplitude of the first sample of the memory being switched into the output function will substantially match the amplitude of the last sample of the memory which is immediately in its output function; and (3) the slope of the first samples of the memory being switched into the output function will substantially match the slope of the last samples of the memory which is immediately in its output function. Additionally, limits are placed on the amount of time that the conditions (2) and (3) are permitted to be in force.

The values of the last two signal samples of the memory which is immediately units output function are communicated to the positive and negative inputs of a subtraction amplifier element 170 for the purpose of calculating the slope of the trailing portion of the identified signal segment. Similarly, the values of the first two signal samples of the memory which is preparing for its output function are communicated to the positive and negative inputs of a subtraction amplifier element 172 for the purpose of calculating the slope of the leading portion of that identified signal segment. The output from said subtractive amplifier 172 is compared with the output of said subtractive amplifier 170 at the hysteresis comparator 176. The comparator output will be in a LO state only when the slopes are nearly equivalent. The output of comparator 176 is inverted in the NAND device 178, the output of which is directed to the OR device 180. The OR device 180 has another input arising from ripple counter 184. This lead will cause the OR device 180 to produce a logical HI state after a predetermined time, whether or not the slope matching conditions have been satisfied. The ripple counter 184 is driven by pulses arising from clock 'F' 87 of FIG. 5, and is reset to a zero count state at each switching of the memory functions by primary switch driver 89 of FIG. 5.

The amplitude values are compared in a similar manner. The value of the leading sample of the memory being prepared for input is communicated by signal line 166 to one input of comparator 186. The amplitude of the trailing sample of the memory in immediately in its output function is communicated by signal line 162 to the reference input of comparator 186. The output of comparator 186 will be in a LO state when the amplitudes are nearly equivalent. The output of comparator 186 is then inverted in the NAND device 188, the output of which is directed to the OR device 190. The OR device 190 has another input arising from ripple counter 184. This other input will cause the OR device to produce a logical HI state after a predetermined time, whether or not the amplitude matching conditions have been satisfied.

The outputs from the OR devices 180 and 190 are directed to an AND device 192. A HI output is produced on AND device 192 when the slope and amplitude conditions, or their time default conditions have been achieved. Output from AND device 192 serves as one of the inputs to a final AND device 198. The other input to AND device arises from flip-flop device 194. The flip-flop device 194 will be caused to obtain a HI state upon receiving a pulse from the ripple counter 184. Said enabling pulse will occur in accordance with a predetermined number of pulses of clock 'F' 87 of FIG. 5 which correspond to the number of storage locations in the memory. A reset pulse will arising from the primary switch driver 89 of FIG. 5 causes the flip-flop device 194 to revert to a LO state when the memory functions are changed. A logical HI value on the output of AND device 198 corresponds to deglitch conditions being achieved.

ALTERNATIVES TO THE PREFERRED EMBODIMENT

While the various elements, groups and circuits shown in the preferred embodiment of the preceeding FIGS. 3 through 5 and FIGS. 7 and 8 provide a sufficient system for performing the generalized signal processing subject to this invention, it should be readily apparent that optional circuitry can be used to accomplish the various funcitons. Further, future selection and utilization of the various alternatives is subject to the direction and development of generic technologies. Several examples employing alternative contemporary technologies to the above described preferred embodiment are presented.

The memory devices used in the several delay lines 83, 108, 130 and 144 are discrete-time analog devices which could be replaced by digital storage elements and the appropriate analog-to-digital conversion elements. The inverse conversion of the digital-to-analog signal would also be required. The band splitting functions which are indicated by analog band filters could be accomplished by digital filtering techniques such as finite impulse response (FIR) or other transversal digital filters. The adaptive noise cancelling filter of FIG. 7 can be accomplished in a variety of ways from very simple phase-locked-loop circuits to the use of digital computation on the input signal using preprogrammed pattern comparison algorithms. The nonlinear amplifier element demonstrated in FIG. 5 is a double sided logarithmic amplifier, however many other amplifiers could serve appropriately. In this regard the first stage of a recording enhancing device (commonly called "Dolby") such as a Signetics Corp. NE570N could serve adequately. Finally, a variety of circuit noise reduction schemes such as parallel processing of inverted signals (common mode rejection) might advantageously be employed. The various advantages of the aforementioned alternatives would be determined as much by cost and component count factors as by technical improvement of the signal processing quality to be accomplished. In this regard the aforementioned alternatives are included herein for the sake of completeness, and such improvements in circuitry should be obvious to those skilled in the application of digital and analog electronic integrated circuitry.

RELATIONSHIP TO THE PHYSIOLOGICAL PROCESS OF HEARING

Referring now to the various FIGS. and particularly to FIG. 3, attributes of the invention will be demonstrated by describing the function of each element as it relates to the enhancement of or substituion for the variety of lost physiological processes characteristic of hearing deficiency.

In operation the auditory signal is transduced into an electrical signal by the microphone 40 and the buffer amplifier 42 in a conventional manner. The adaptive noise cancelling element 44 provides a means for separating the meaningful portion of the auditory signal from noise, a function which is normally provided by the neural feedback in the ear. The obfuscation of meaningful information by the addition of competing signals is called masking, and in patients having any neural hearing deficit, the ability to derive information in the presence of masking is compromised. The placement of the adaptive noise cancelling element 44 near the front end of the signal processing therefore provides an automatic means for compensating for lost masking definition.

The next element in the illustrated signal processing series is an automatic gain control element 45, and it serves the purpose of variously enhancing and suppressing the energy of the acoustic signal. Its physiological counterpart in the auditory system is bones of the middle ear, and also in the neural threshold alteration which occurs at the mechanical-to-neural transduction site. In some particular individuals the automatic gain control element 45 also would find application to severely retard signal strength due to hyper-sensitivity to signals which occur as a result of depressed neural thresholds from certain pathologies of cellular electrolytes.

The band separating network 46 provides the means for directing specific frequency ranges of the auditory signal through the processing of the remaining signal modification networks 50. Since the perception of the auditory signal occurs on a frequency-by-frequency basis, and because the loss of hearing is directly related to the failure of certain cells which are responsible for certain frequencies, any alteration of the auditory signal must also be performed in recognition of the unique frequency/pathology relationship. The band separating network 46 performs such a function. The specific number of bands is dependent upon the pathology of the individual and also is limited to an upper number by linguistic considerations. For example an individual having simple high frequency loss might only require severe modification of the frequencies contained in a single frequency band from 2500 to 3500 Hz whereas another individual with the capacity to hear only ten distinct tones over the entire auditory range might require ten bands, with each generating the single audible tone.

The signal which is transmitted in each selected band is directed through a signal modifying network 50. Within each of these networks are four distinct elements for performing specific signal alteration in order to optimize the transmission of information contained in the signal over those neural structures which remain viable. The bandlimited signal is caused to be processed through a nonlinear amplifier element. This element provides for the greater amplification of small amplitudes of the signal while suppressing the larger amplitudes. The effect of such processing tends to promote the effect of sound energies of low power which have significant information content such as the consonants "v" and "f". Such singular devices have been various called speech compressors or peak clippers. The detection of the crossing of zero is of much greater importance than is the determination of the amplitude of the vibrating source as far as the determination of linguistictly significant events is concerned.

After the band limited signal has been caused to pass through the nonlinear amplifier element 52, it enters the harmonic frequency transposer element 54. In the harmonic frequency transposer element the band limited signal is shifted in frequency, while retaining all of the harmonic relationships in the original signal. Applicant believes that such harmonic retention is significant to the optimization of neural cues for recognizing auditory patterns. The effect of the shifting process is to redirect portions of the auditory signal from neurally dead frequencies to those neural channels which remain viable to the transmission of particular frequencies. Shifts which are made in this manner should be performed only enough to cause enhanced neural cues since distortion of the auditory signal rises significantly with large shifts. However, there is far greater tolerance of shifts in the frequencies above about 2000 Hz than there is in the lower frequencies.

The bandfilter element 55 which receives the transposed bandlimited signal serves to limit the energy which will drop below the lower frequency limit of the original band limited signal. The bandfilter element 55 may also be used in a narrow band manner to provide an acoustic cue representing the entire energy content of the band for those cases where an individual retains only sensitivity for a few tones in the entire auditory spectrum. The signal which is directed into bandfilter element 55 emerges from through a gainshaping amplifier 56 to provide a final degree of tuning to the signal. This last mentioned element 55 may be used to compensate for subtle differences in the sensitivities of neural hair cells and structures to mechanical excitation.

While the elements represented are required for the most general case of signal processing, their function may be so adjusted to provide no net effect if it is not required. Similarly, the sequence of the functions may also be performed in other than the order described herein.

The separately processed signal bands 50 are next summed together with various intensity weightings being applied by potentiometers 58 at summing amplifier 59. It is necessary that equivalent time delays be provided in each of the signal bands prior to their recombination.

It is readily apparent that if all elements in any of the signal modifying networks 50 except the frequency transposer element 54 are shunted with regard to the signal path, and if both clock 'S' 86 and clock 'F' 87 rates are made equal, a pure delay is imposed on that portion of signal traversing said network. By further requiring that all of the clock 'S' 86 rates be made equal in all of the individual signal modifying networks 50, the said delayed signals would provide for the temporal or phase matching of all signals processed in the plurality of signal modifying networks 50 of FIG. 3.

So similarly may other combined sets of parameters in the various elements provide yet other special cases. For example, the total energy content of an entire frequency band may be represented as a narrowband signal of harmonically related information by a suitable choice of transposition, filtering, and heterodyning.

DIAGNOSIS AND TREATMENT OF HEARING LOSS

Diagnostic methods for the treatment of hearing loss employing the means recited above require a significant departure from contemporary audiological practice.

In contemporary audiology, the pure tone audiogram is a primary method for evaluating auditory function. This evaluation is performed by presenting the listener with a single-frequency signal and incrementally increasing or decreasing the intensity of the signal. The listener indicates when the tone is audible, and when he indicates that the sound is not audible, a threshold of hearing is established for that tone. Then the process is repeated at typically six or eight more frequencies spaced at approximately one octave intervals. At the conclusion of the test, an "audiogram" is constructed by joining the test points. It is common practice for these straight line segments to be drawn on either semilogarithmic or double logarithmic coordinates. These very qualitative graphs are generally interpreted as a representation of the filter characteristics of the listener's auditory system.

A substantially more accurate charcterization of the auditory system filter characteristics is obtained by presenting the listener with a constant intensity signal which is caused to vary monotonically in frequency. As the signal slowly sweeps across the sonic frequency range, it is progressively presented to individual hair cell groups. As long as there is a normal neural structure and function, the listener responds to appropriate threshold intensity levels. When pathologies affect a particular site along the basilar membrane, a sudden "dropout" of the threshold sensitivity occurs, and the listener fails to respond. The intensity level is subsequently raised, and a second identification of the "dropout" is obtained. The procedure is repeated at higher intensity levels, with the frequency ranges of the sweeps narrowed to minimize uncomfortably loud signals from being addressed to normal portions of the mechanoneural network.

The recording of the listener's response can be automated using a conventional X-Y plotter which has a pen lifting device. The intensity level is represented as a voltage on the "Y" input to the plotter, and the frequency is represented as a voltage on the "X" axis to the plotter. The patient causes the pen of the plotter to lift by depressing an electrical switch. As the sound is administered to the patient in a slowly increasing frequency, a constant intensity a line will be drawn across the plotter. In those regions where hearing is lost, the pen will be lifted, and the line will be caused to discontinue. Then the intensity is increased, and a second line is drawn. This process is continued until a filter characteristic of the patient's auditory system is established.

The sweeping of frequency at a constant intensity is a most important alteration to the generation of a filter characterization of the ear. First, since hearing is sensed on a frequency by frequency basis, the method permits frequency resolution of the "filter" not otherwise possible. Second, the method minimizes "recruitment" effects on the filter characterization. Applicant postulates that recruitment, a condition in which a sudden onset of hearing occurs upon the presentation of a gradually increasing stimulus intensity, arises when hair cells adjacent to regions of pathology are suddenly brought above their transmitting threshold. Finally, the method enables the identification of the very narrow bands of frequency reception which may be present in persons who are profoundly deaf to pure tone stimuli which are not addressed to the viable frequencies.

The accurate characterizaton of the listener's auditory channels permits a ranging of the variable parameters of a master generalized signal processing hearing aid. The number of separate channels which are used for the signal processing is dependent upon the number of dropouts in the listener's frequency response, their position along the frequency axis, and their magnitudes. The number and frequency position of the separated channels is also influenced by the phonemic requirements of language.

After the initial signal processing channels are determined using the sweep frequency audiogram, an initial set of values are chosen for the various gains and gain-shaping elements. The listener is then presented with well known word discrimination lists, i.e. spoken words which are known to differ in subtle ways from other words, and his test scores are taken. On the basis of the types of words that are missed and the spectral content of those words, the appropriate gain changes, and if necessary transposition placements and characters are altered. The listener is also an active participant in this alteration of parameters portion of hearing aid prescription.

Next, a competing noise signal is added to the background against which the listener is presented the word discrimination tests. The characteristics of the noise cancelling and automatic gain control portions of the master hearing aid are adjusted to provide a maximal response to these tests. Again the parameter adjustment is made with the active participation of the listener in the adjusting procedures.

A fine tuning process is the final step in determining the the general signal processing required for an individual listener. During this final phase, a series of prerecorded words representing a variety of adult male, adult female and child's voices are presented. The ranging of parameters responsive to distinguishing language spoken by these voices is determined, and these parameters become the final prescription for an individual hearing aid.

While a specific embodiment and method for the purpose of the invention has been disclosed, and alternatives to certain elements and procedures have been suggested, it will be appreciated that although each of the illustrated elements and suggested steps is desirable for the most generalized signal processing, some of these elements or steps may be so adjusted to produce no net effect, or in special cases, some elements or steps may be eliminated entirely. Similarly, it will be appreciated that the sequence of individual signal processing elements also may be permuted to address individual cases. It will be further appreciated that other circuits to implement the elemental functions will be known to those skilled in the art and are to be understood as within the scope of the invention as defined in the appended claims.

I claim:

1. A signal processing apparatus for modifying acoustic patterns, comprising:
    (a) means for receiving an acoustic signal and generating a processed signal in response thereto, said generated processed signal being representative of the acoustic signal;
    (b) adaptive noise cancelling means associated with said receiving and generating means for suppressing portions of said generated signal which do not exceed a predetermined pattern recognition function, and producing an output signal characteristic thereof;
    (c) frequency band separating means for dividing said generated signal into at least two separated signals in accordance to frequency;
    (d) means for selectively transposing the frequency of at least one of said separated signals separated by said frequency band separating means;

(e) means for providing temporal matching of said separated signal;
(f) means for summing the temporally matched signals into a resultant signal; and
(g) means for converting said amplified signal into an acoustic signal.

2. An apparatus for minimizing transitional discontinuities arising from the joining of originally discontiguous signal segments, comprising:
(a) means for comparing the magnitude of the trailing edge of a first signal segment with the magnitude of the leading edge of a succeeding signal segment;
(b) means for determining the rate of change of said first signal segment's magnitude at the trailing edge;
(c) means for determining the rate of change of said succeeding signal segment's magnitude at its leading edge; and
(d) means for generating an output signal upon the substantial correspondence of both the magnitude and rate of change of said trailing edge of said first signal segment with the magnitude and rate of change of said leading edge of said succeeding signal segment.

3. An apparatus as recited in claim 2 further including means for generating an output signal only upon the substantial correspondence of both the magnitude and rate of change of said trailing edge of said first signal segment with the magnitude and rate of change of said leading edge of said succeeding signal segment and the occurrence of a further signal.

4. An apparatus as recited in claim 2 further including a sequential memory element wherein said magnitude comparing means and said first signal rate of change determining means are responsive to said sequential memory element.

5. An apparatus as recited in claim 4 further including alternate memory means for sampling and storing the trailing and next-to-trailing portions of a signal in said sequential storage element.

6. An apparatus as recited in claim 5 wherein said magnitude comparing means and said succeeding signal rate of change determining means are responsive to said alternate sampling and storing means.

7. An apparatus as recited in claim 5 further including switching means for alternately connecting each of said sampling and storing means to the trailing and next-to-trailing storage locations in said sequential storage element and simultaneously outputting the other of said alternate sampling and storing means to both of said magnitude comparing means and said rate determining means for said trailing edge of said first signal segment.

* * * * *